(12) United States Patent
Powley et al.

(10) Patent No.: US 8,079,990 B2
(45) Date of Patent: Dec. 20, 2011

(54) IMPLANTABLE CATHETER PORT

(75) Inventors: Nicholas R. Powley, Saint Paul, MN (US); Graig Leonard Kveen, Maple Grove, MN (US); Donald Geer, Queensbury, NY (US); Steven Allex, Shoreview, MN (US); John Arthur Zawacki, Shorewood, MN (US)

(73) Assignee: R4 Vascular, Inc., Hoboken, NJ (US)

( * ) Notice: Subject to any disclaimer, the term of this patent is extended or adjusted under 35 U.S.C. 154(b) by 0 days.

(21) Appl. No.: 12/135,965

(22) Filed: Jun. 9, 2008

(65) Prior Publication Data

US 2009/0099526 A1    Apr. 16, 2009

Related U.S. Application Data

(60) Provisional application No. 60/942,722, filed on Jun. 8, 2007.

(51) Int. Cl.
*A61M 37/00* (2006.01)
(52) U.S. Cl. ......... 604/288.02; 604/288.01; 604/288.03; 604/288.04; 604/890.1; 604/891.1
(58) Field of Classification Search .............. 604/288.01–288.04, 890.1, 891.1, 604/167.01–167.04
See application file for complete search history.

(56) References Cited

U.S. PATENT DOCUMENTS

| | | | |
|---|---|---|---|
| 5,041,098 A | 8/1991 | Loiterman et al. | |
| 5,399,168 A * | 3/1995 | Wadsworth et al. | 604/175 |
| 5,704,915 A | 1/1998 | Melsky et al. | |
| 5,713,859 A | 2/1998 | Finch, Jr. et al. | |
| 5,755,780 A | 5/1998 | Finch, Jr. et al. | |
| 6,962,577 B2 * | 11/2005 | Tallarida et al. | 604/288.02 |
| 6,997,914 B2 | 2/2006 | Smith et al. | |
| 7,351,233 B2 | 4/2008 | Parks | |
| 7,445,614 B2 | 11/2008 | Bunodiere et al. | |
| 2006/0058744 A1 | 3/2006 | Tallarida et al. | |
| 2006/0084929 A1 | 4/2006 | Eliasen | |
| 2006/0100592 A1 * | 5/2006 | Eliasen | 604/288.02 |
| 2006/0178647 A1 | 8/2006 | Stats | |
| 2006/0184141 A1 | 8/2006 | Smith et al. | |
| 2006/0264898 A1 | 11/2006 | Beasley et al. | |
| 2007/0073250 A1 | 3/2007 | Schneiter | |
| 2008/0086099 A1 | 4/2008 | McKinnon et al. | |

FOREIGN PATENT DOCUMENTS

WO    WO 01/41858 A2    6/2001
WO    WO 01/41858 A3    6/2001

* cited by examiner

*Primary Examiner* — Bhisma Mehta
*Assistant Examiner* — Larry R Wilson
(74) *Attorney, Agent, or Firm* — DLA Piper LLP (US)

(57) ABSTRACT

A single or multi-port vascular access device including one or more reservoirs each covered by a needle-penetrable, self-sealing septum. The one or more reservoirs each open to an outlet in a stem to which the catheter is attached. The reservoir may be generally circular or ellipsoid in shape and large enough so that fluid movement into and out of the needle is unimpeded. In order to maximize flow between the reservoir and catheter and to minimize any regions of impeded or low fluid flow where coagulation or cell shearing may occur, the fluid passage leading from the reservoir through the outlet into the catheter is defined by unique tapered and tangential geometries. For example, the outlet surface may be globally tangent along the entire reservoir surface, or may be globally tangent along only one side of the reservoir surface.

23 Claims, 13 Drawing Sheets

1

IMPLANTABLE CATHETER PORT

CROSS REFERENCE TO RELATED APPLICATION(S)

This application claims the benefit of priority under 35 U.S.C. §119(e) of U.S. Ser. No. 60/942,722, filed Jun. 8, 2007, the entire content of which is incorporated herein by reference.

BACKGROUND OF THE INVENTION

1. Field of the Invention

The present invention relates generally to vascular access devices and more specifically to subcutaneously implanted catheter ports.

2. Background Information

A variety of implantable devices, known as subcutaneous ports, are utilized to administer therapies that require central venous access through a non-coring needle received by the port, obviating the need for transdermal central venous catheters. For applications such as bodily fluid exchange and/or removal therapies, drug delivery, pheresis, hemofiltration, hemodialysis and other applications that must be periodically repeated, subcutaneous ports are preferable to other methods of accessing a patient's vascular system, such as direct percutaneous introduction of a needle through the patient's skin into a blood vessel or use of transcutaneous catheters.

A variety of subcutaneous ports have been previously described. A subcutaneous port has one or more reservoirs, each covered by a needle-penetrable, self-sealing septum. The reservoir opens up to a stem which connects to a catheter. Current ports 100, an example of which is shown in FIG. 3, have a small round outlet hole 106 exiting the side of the reservoir 102 and a stem 104 defining an outlet extending from that hole 106. All the edges and corners resulting from the outlet 106 create dead-zones, where blood and other fluids traversing the port 100 may stagnate. Acute edges and surfaces that confer abrupt directional changes in the fluid flow through the internal regions of the port lead to dead-zones, cell shearing, platelet activation and clotting.

The buildup of blood or fluid is known as sludge, and limits the ability of the port to provide fluid flow in and out of the port, reducing the effectiveness, safety and overall useful life of the port. If the port is used to transfuse blood, blood trapped in these dead spaces has the tendency to form clots and block the flow of fluid through the reservoir. An additional limitation of existing designs is that the edges and corners of current designs also prevent the passage of wires through the port to clear a blockage.

Accordingly, there has been a need for an improved implantable, subcutaneous single or multi-port vascular access device for bodily fluid exchange therapies and other drug delivery applications, which include specific geometries exhibiting, for example, increased port patency, reduced dead-flow zones, and increased mixing within the port. Additionally, there has been a need for vascular access devices that are inexpensive, more comfortable, longer lasting, and easier to locate within the patient's body and suitable for both low and high volume transfer of fluids.

SUMMARY OF THE INVENTION

The present invention is based on the discovery of unique geometries for subcutaneous vascular access ports having improved flow properties.

Accordingly, the present invention provides a subcutaneous single or multi-port vascular access device. The device includes a port body including a reservoir and an outlet in fluid communication. The shape of the reservoir and the outlet are defined by the inner surface of the port body having opposed sidewalls which, for convenience, shall be referred to herein as an inner an outer sidewall forming lateral boundaries and defining a flow passage along the reservoir toward the distal tip of the outlet. The inner sidewall may be globally tangent along the reservoir surface, in its entirety or part thereof, and the outer sidewall is tapered from the reservoir to the distal tip of the outlet.

The ports of the present invention include one or more reservoirs covered by one or more needle-penetrable, self-sealing septums. The reservoir(s) collectively open to an outlet to which a catheter may be attached at the distal tip of the outlet. Accordingly, in one aspect, the port may be used with either a fixed or detachable catheter, with the outlet having the appropriate shape to connect with the catheter.

The ports incorporated in the vascular access devices of the present invention exhibiting improved flow properties encompass various geometries. In one aspect, the internal shape of the port body defining the flow path of the reservoir and outlet is such that the outer sidewall transitions from the reservoir to the outlet defined by a radius of curvature R1 and extends to the distal tip of the outlet.

In another aspect, the internal shape of the port body defining the flow path of the reservoir and outlet is such that the outer sidewall transitions from the reservoir to the outlet defined by a radius of curvature R1 and linearly extends to the distal tip of the outlet.

In one aspect, the internal shape of the port body defining the flow path of the reservoir and outlet is such that the outer sidewall transitions from the reservoir to the outlet defined by a radius of curvature R1 and extends arcuately at a constant radius to the distal tip of the outlet.

In another aspect, the internal shape of the port body defining the flow path of the reservoir and outlet is such that the outer sidewall transitions from the reservoir to the outlet defined by a radius of curvature R1 and extends curvilinearly to the distal tip of the outlet. Accordingly, the internal shape of the port body defining the flow path of the reservoir and outlet may be such that the outer sidewall transitions from the reservoir to the outlet defined by a radius of curvature R1 and extends curvilinearly on a path defined by multiple radii, Rn. In a preferred aspect, the outer sidewall transitions from the reservoir to the outlet defined by a radius of curvature R1 and extends curvilinearly on a path defined by one additional radius R2 or two additional radii R2 and R3.

In yet another preferred aspect, the internal shape of the port body defining the flow path of the reservoir and outlet is such that the outer sidewall transitions from the reservoir to the outlet defined by a radius of curvature R1 and extends to the distal tip of the outlet on a splined path.

The vascular access devices of the present invention may include a single port or include multiple ports. In a preferred aspect, the multi-port device includes two ports, however, more than two ports may be incorporated into the device. In a device that includes multiple ports, the ports may be identical in shape, mirror images, or of different shape.

In one aspect, the reservoir is a chamber that may be generally ellipsoid or circular in shape. However, the reservoir may be of any smoothly curved shape which attributes improved flow rate and mixing of the fluid in the reservoir. In one aspect, the reservoir is large enough so that fluid movement into and out of the needle is unimpeded and small enough to keep the flow rate up and to use a minimal amount of fluid for flushing.

The present invention provides a vascular access device having a reservoir and outlet shaped such that the flow is maximized from the reservoir through the outlet into the catheter. In one aspect, at least the outer outlet sidewall is globally tangent along the entire reservoir surface, or the inner sidewall surface so that the reservoir/outlet (the cavity) has, for example, generally a teardrop shape. In another aspect, only the outer outlet sidewall is globally tangent along only one side of the reservoir surface so that the cavity has generally a nautilus shape, which has the benefit of promoting circular motion within the cavity. In a preferred aspect, the outlet's outer sidewall surface is globally tangent along one side of the reservoir and tapered along the opposing inner sidewall.

The reservoir's internal cavity surface is smooth and broad to minimize any sources of impeded flow in order to minimize regions of low flow where coagulation may occur. In one configuration, however, the floor of the internal surface of the reservoir cavity is dimpled to minimize the volume of fluid that may collect in the central region of the reservoir cavity.

In one further aspect, in order to increase flow between the needle and the reservoir and to reduce the regions of low flow in the reservoir, the underside of the septum is concave to match the curve of the reservoir. In another aspect, a dimple in the septum that generally mirrors the bottom of the dimpled reservoir configuration results in a cross-sectional shape that minimizes where blood flow is reduced and coagulation may occur. In yet another aspect, one or more dimples may be off center and configured such that the height does not inhibit the flow of fluid from the needle.

The edge of the reservoir body surrounding and adjacent to the septum is designed to be tactilely identifiable through the skin. In one aspect, the edge is raised above the level of the septum. The edge may have a radius that is small enough to be easily sensed through the skin, but large enough for patient comfort and prevents skin erosion. Alternatively, the septum 18 may be raised above the edge of the port 70 as shown in FIG. 6.

The vascular access device of the present invention is suitable for use with various designs of catheters depending on the particular application desired. For example, the distal end of the catheter may be terminated by any type of tip configuration that is desired, such as blunt, step, and split tips. In one aspect, the tip configurations include those that have comparable forward and reverse flow. In another aspect, the catheter may be tapered from its attachment point to the tip of the outlet 22 along the length of the catheter. The taper may travel the entire length of the catheter or any portion thereof.

The vascular access device of the present invention may include a port body that is fabricated from a single piece of stock material as one unitary piece. However, in a preferred aspect, the port body includes at least two pieces separately fabricated, wherein one of the pieces does not include the septum. Accordingly, a port body of a device of the present invention is made by a process that includes: a) separately forming at least two pieces; and b) joining the pieces together thereby defining the surface of the reservoir and outlet. In a preferred aspect, two pieces are separately formed, including for example, an upper piece and a bottom piece.

The upper and bottom pieces of the port body are preferably each of unitary construction, each being formed from a single piece of stock. Alternatively, the pieces may be formed from stock of multiple types of materials. When joined together, both the upper and bottom pieces form the entire reservoir/outlet configuration and may also form additional features, such as an elongated outlet stem including means for attachment to a catheter. Such means may include locking features, such as ribs or barbs being incorporated on the outside of the elongated stem.

DETAILED DESCRIPTION OF THE INVENTION

The present invention derives from the discovery that providing a globally tangential, preferably tapered tangential, transition from a vascular access port to its outlet port will significantly improve the flow properties of the device. Fluid flow and resistance through the port body to the catheter are critical factors in preventing dead-zones and cell shearing leading to clotting in fluids such as blood. Accordingly, the present invention provides a vascular access device including uniquely shaped ports designed to improve fluid flow and mixing thereof through the port.

Figure 1:
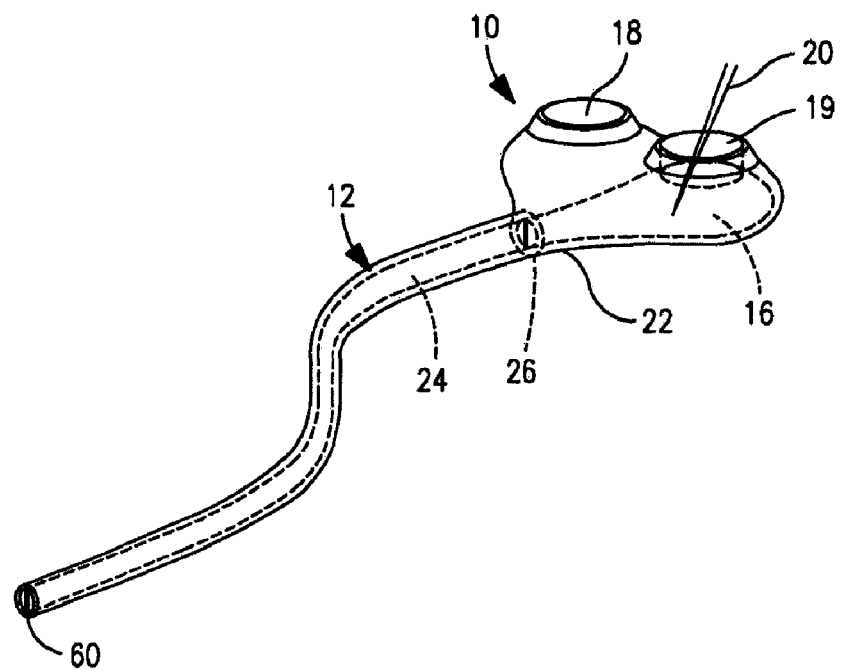
FIG. 1 is a perspective view of one embodiment of a port of the present invention including a catheter.
Figure 2:
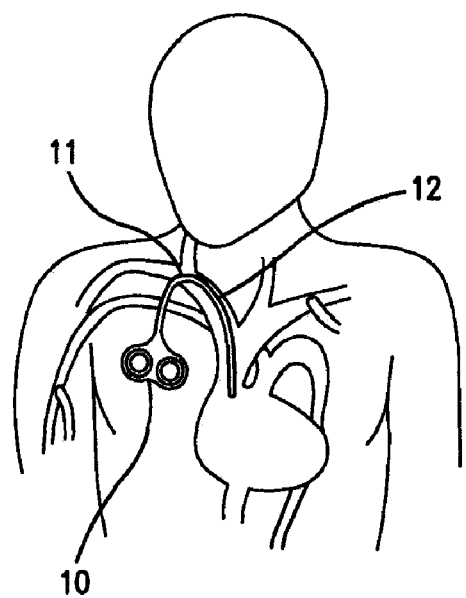
FIG. 2 shows the traditional location of a port within the body.
Figure 3:
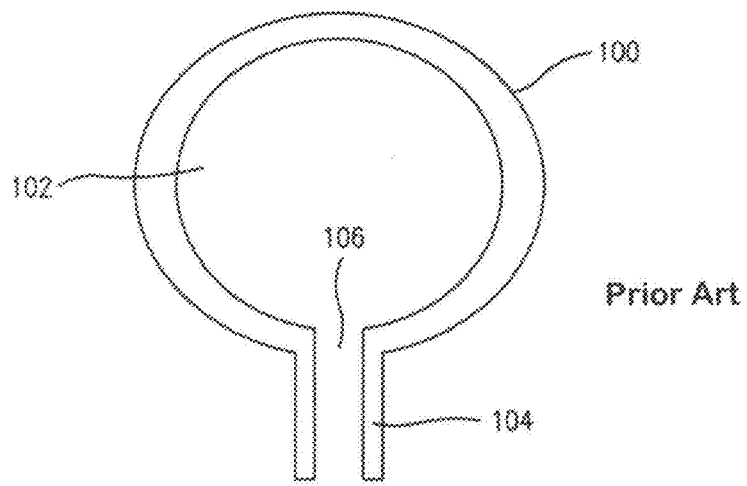
FIG. 3 is a cross-sectional view of a port of the prior art.

In one embodiment, the present invention is a vascular access device for subcutaneous implantation including a port 10 for use with a catheter 12 connected to the port 10, as shown in FIG. 1. As shown in FIG. 2, the port 10 is implanted under the skin and the catheter 12 gains access to the vasculature through a vascular puncture 11, which may or may not be a significant distance from the location of the port 10.

Increased patient comfort following subcutaneous implantation is enhanced by smoothing all of the outer surfaces of the port, while maintaining a flat bottom for location within the body. While the port of the present invention is preferably constructed out of durable materials, such as metals, alloys, and the like, the port of the present invention is designed with minimal stress raising geometries so that the port can be made from less strong materials, such as plastics, while retaining all aspects of longevity and functionality. In a preferred aspect, the port is constructed from polysulfone or delrin. Additionally, the internal surface of defining the reservoir and the outlet may further include various types of coatings. For example, when plastics are used to construct the port, internal coatings, such as alloys or metals, may be employed to protect the internal surface from being scratched or deformed by the needle. In a preferred aspect, the internal surface is chromed.

A variety of plastics and/or polymeric materials are well known in the art and suitable for use in subcutaneous applications such as the device of the present invention. One advantage of plastics is that most are compatible with magnetic resonance imaging (MRI). Plastics are generally non-conducting, so that, during an MRI procedure, eddy currents that greatly reduce the quality of the MRI image at the location of the metallic/conducting material are significantly reduced. Additionally the metal parts heat up and may cause tissue damage.

The reservoir 16 is a chamber that is generally ellipsoid or circular in shape, but maybe be any smooth curved shape that improves fluid flow. The ellipsoid may be wider than it is high, circular, or higher than it is wide. The minimum height of reservoir 16 is such that there is sufficient room so that fluid movement into and out of the side hole of the Huber needle is unimpeded. The reservoir 16 cannot be too large otherwise the fluid flow rate is not high enough to clean the walls on flushing, as described below. Another parameter for the size of the reservoir 16 is the desire to be able to flush the system with a minimal amount of saline or other flushing fluid, on the order of about 10 ml of fluid.

As shown in FIGS. 4-11, and 15-18 the vascular access device of the present invention includes both single and multi-port embodiments. The port of the present invention 10 has a body 14 with one or more reservoirs 16, each covered by a needle-penetrable, self-sealing septum 18, through which fluid(s) is injected into or removed from the reservoir 16 via a needle 20. The septum 18 is typically, though not necessarily, composed of a biocompatible material, such as silicone. In varying aspects, the needle 20 may be textured, slightly bent, or be of varying diameter along its length to help it resist the pressure imposed during the procedure. Textures may include increasing the general surface roughness and small cuts or ridges (in hoops) around the needle.

A variety of needle designs may be used in combination with the present invention. In one aspect the needle is a blunt tipped needle that may be introduced over a trocar. In a preferred aspect, fluid is expelled from the tip of the needle and directed toward the bottom of the reservoir such that the fluid is deflected from the bottom surface creating a vortex or torroidal flow.

The reservoir 16 opens up to an outlet 28 defining a flow passage through the reservoir 16 and the aperture 26 at the distal tip of the outlet 28 to which the catheter 12 is attached. The combination of the reservoir 16 and bore through outlet 28 defines the totality of the open space in the port and is identified herein as "the cavity." Fluid moves between the catheter lumen 24 and the outlet 28 via an aperture 26 at the distal tip of the outlet 28.

The port body 14 includes a reservoir 16 and an outlet 28 in fluid communication having defined geometries for maximizing fluid flow through the defined flow passage. Therein the shape of the reservoir 16 and the outlet 28 (together, the cavity) are defined by the inner surface of the port body, including an inner sidewall 100 and an outer sidewall 110 forming lateral boundaries defining a flow passage along the reservoir 16 to aperture 26 at the distal tip of the outlet 28 (see, for example, FIGS. 8-9, 16 and 18). In various aspects, the inner sidewall 100 is globally tangent along the reservoir surface and the outer sidewall 110 is tapered from the reservoir to the distal tip of the outlet. As used herein, a taper means a smooth and gradual diminution or decrease of diameter or width in an elongated object, such as the flow passage defined by the reservoir and outlet, and may be defined by one or more of a variety of geometries, such as arcs, curves, splines, straight lines, and the like.

Figure 4:
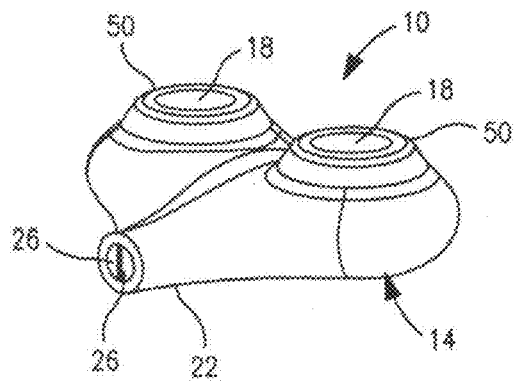
FIG. 4 is a perspective view of one embodiment of a dual port device of the present invention.
Figure 5:
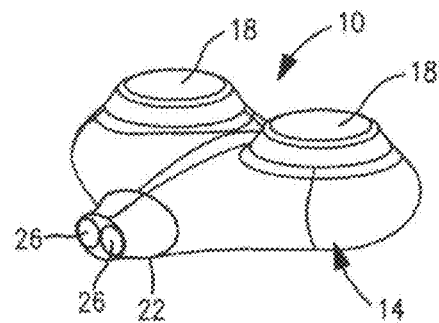
FIG. 5 is a perspective view of another embodiment of a dual port device of the present invention.
Figure 6:
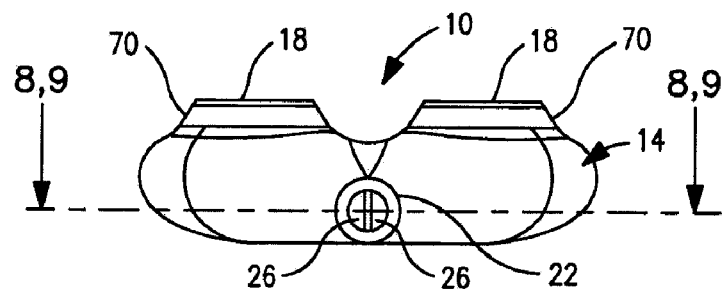
FIG. 6 is a front plane view of the port of FIG. 4.

In one aspect, the stem 22 and aperture 26 are shaped to enable attachment of the catheter 12 to stem 22, and so their diameters are dictated by the catheter parameters, including the size and shape of the cross-section of the associated catheter lumen 24, which may include shapes such as those shown in FIGS. 4 and 5. A variety of other catheter shapes are known in the art and are contemplated for use with the present invention.

The outlet 28 is shaped to maximize flow between the reservoir 16 and the catheter lumen 24. For example, in the outlet 28 of FIG. 8, the outlet surface 36 is globally tangent along the reservoir surface 30. That is, the reservoir surface 30 transitions smoothly and without discontinuities to the outlet surface 36 throughout the circumference of the transition. As a result the shape of the reservoir 16/outlet 28 combination in FIG. 8 resembles an inverted teardrop.

Figure 9:
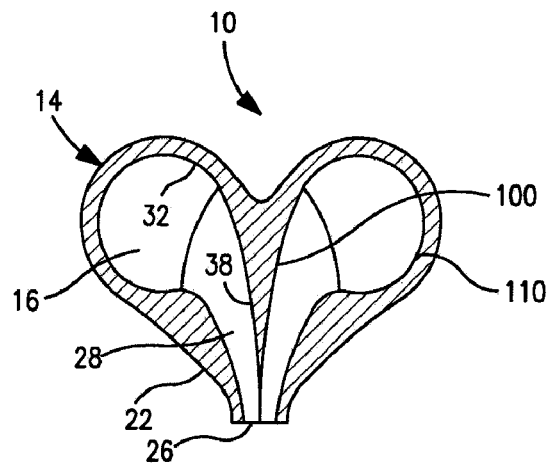
FIG. 9 is a cross-sectional view of another embodiment of the dual port device taken along the line 9-9 of FIG. 6.

In the outlet of FIG. 9, the outlet surface 38 is globally tangent along only one side of the reservoir surface 32, rather than the entire surface 32. That is, the reservoir surface 32 transitions smoothly to the outlet surface 36 throughout only part of the circumference of the transition. As a result the shape of the reservoir 16/outlet 28 combination resembles a nautilus. One benefit of the nautilus shape, as well as other shapes of the present invention, is that it promotes circular motion of fluid within the cavity. Circular motion means that the fluid moves within the entire cavity, rather than there being dead spots, resulting in a better flushed cavity, reducing clotting, and improving fluid flow.

FIGS. 15-19 show preferred embodiments where the flow path between the reservoir 16 and the distal tip of the outlet 28 is defined such that the inner sidewall 100 is globally tangent along the reservoir surface and the outer sidewall 110 is tapered from the reservoir to the distal tip of the outlet. In one aspect, the internal shape of the port body defining the flow path of the reservoir and outlet is such that the outer sidewall 110 transitions from the reservoir 16 to outlet 28 defined by a radius of curvature R1 and extends to the distal tip of the outlet 28.

While keeping the inner sidewall 100 globally tangent along the reservoir surface and the outer sidewall 110 tapered from the reservoir 16 to the distal tip of the outlet 28, in various embodiments, the flow path of the reservoir 16 may be configured by altering the taper of the outer sidewall 110 as it extends to the distal tip of the outlet 28.

As such, in one aspect, the internal shape of the port body defining the flow path of the reservoir 16 and outlet 28 is such that the outer sidewall 110 tapers from the reservoir 16 to the outlet 28 defined by a radius of curvature R1 and linearly extends to the distal tip of the outlet. As used herein, linearly is intended to mean a path that is substantially straight.

In another aspect, the internal shape of the port body defining the flow path of the reservoir 16 and outlet 28 is such that the outer sidewall 110 tapers from the reservoir 16 to the outlet 28 defined by a radius of curvature R1 and extends arcuately at a constant radius R1 to the distal tip of the outlet. As used herein, arcuately is intended to mean a path that is curved or bowed.

Figure 19:
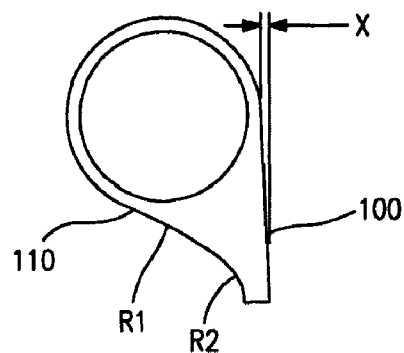
FIG. 19 shows a single port device having a reservoir and outlet configuration that is tapered and tangential.
Figure 20:
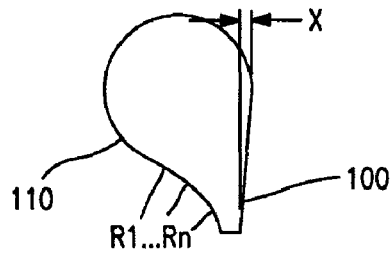
FIG. 20 shows a shows a single port device having a reservoir and outlet configuration that is tapered and tangential.

In a further aspect, the internal shape of the port body defining the flow path of the reservoir 16 and outlet 28 is such that the outer sidewall 110 tapers from the reservoir 16 to the outlet 28 defined by a radius of curvature R1 and extends curvilinearly to the distal tip of the outlet. As used herein, curvilinearly means a path that is characterized by one or more curves defined by one or more radii. Accordingly, a curvilinearly extending taper of the outer sidewall 110 may be such that the outer sidewall 110 tapers from the reservoir to the outlet defined by a radius of curvature R1 and extends curvilinearly on a path defined by multiple radii, Rn as shown in FIG. 20. However, it is more broadly intended here that the term "curvilinear" encompasses a line that may additionally include straight linear segments. In a preferred aspect, the outer sidewall transitions from the reservoir to the outlet defined by a radius of curvature R1 and extends curvilinearly on a path defined by one additional radius R2 or two additional radii R2 and R3 as shown in FIGS. 19 and 20.

In yet another aspect, the taper of the outer sidewall 110 is defined by a radius of curvature R1 and extends to the distal tip of the outlet 28 on a splined path. As used herein, splined means a smooth path characterized by one or more spline functions. For example, in FIG. 21, points (a) and (b) of the outer sidewall 110 define points at which the taper may be altered by different spline functions leading to the distal tip of the outlet 28.

Figure 21:
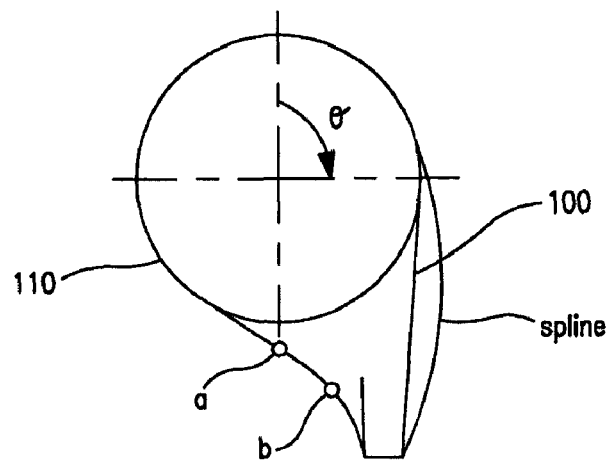
FIG. 21 shows a shows a single port device having a reservoir and outlet configuration that is tapered and tangential.

Throughout the various embodiments wherein the outer sidewall 110 taper is defined by various geometries, the transition from the reservoir 16 to the outlet 28 defined by radius R1 can begin at any point along the outer sidewall 110 as defined by the angle θ as shown in FIG. 21. In one aspect the transition begins where angle θ is between 90° and 360°. In another aspect, the transition begins where angle θ is between 90° and 270°. In various other aspects, the transition begins where angle θ is between 90° and 255°, 90° and 240°, 90° and 225°, 90° and 210°, 90° and 195°, 90° and 180°, 90° and 165°, 90° and 150°, 90° and 135°, 90° and 120°, or 90° and 105°.

To maximize flow, the inner sidewall 100 is globally tangent along the reservoir surface 32. In one aspect the inner sidewall 100 may further include a splined configuration as shown in FIG. 21. Additionally, in the dual port embodiment, the inner sidewall 100 may be tilted a distance X as shown in FIGS. 19 and 20 to allow for the outlets of the dual ports to be 1 catheter wall thickness apart. Accordingly, distance X is determined by the specification of the catheter that is used.

Figure 10:
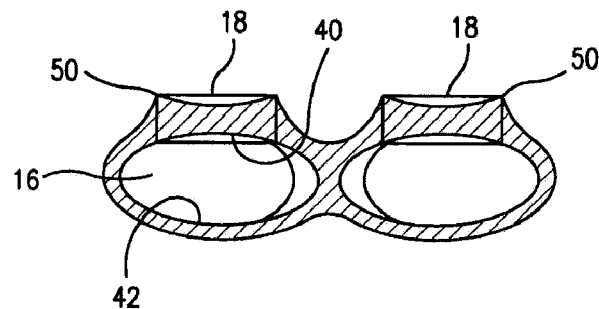
FIG. 10 is a cross-sectional view of an embodiment of the reservoir and an embodiment of the septum taken along the line 10-10 of FIG. 7.
Figure 11:
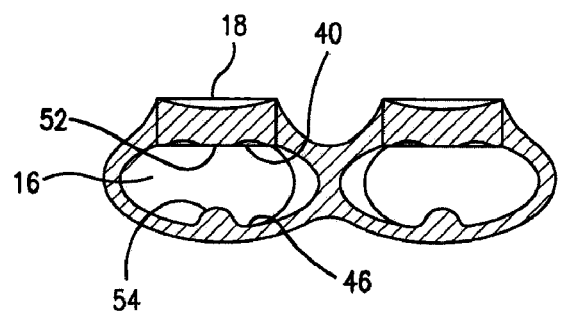
FIG. 11 is a cross-sectional view of another embodiment of the reservoir and another embodiment of the septum taken along the line 11-11 of FIG. 7.

The cavity is shaped to minimize regions of low flow within the port 10 where coagulation may occur. The reservoir 16 of FIG. 10 is smooth and broad to minimize any sources of impeded flow. The reservoir 16 of FIG. 11 is dimpled, as at 34, to minimize the volume in the central region of the reservoir 16 where blood cells may condense and have a propensity for coagulation. Preferably the dimple is not so high as to form a fluid barrier blocking outlet 28 or so high as to block the outlet of the needle.

As noted above, ports of the prior art cannot be cleaned or cleared by wires following use. Thus an advantage of the present invention is that the smoothing of the internal features of the port enables cleaning or clearing with a wire. Additionally, the internal features of the port provides access for additional devices and/or allows additional medical procedures. For example, the port shape allows access to a cytology brush for performing cell sampling with in the internal port structure. In another aspect, electrodes may be passed through the port providing access to the vasculature or heart to determine electrophysiological characteristics. In yet another aspect, the port design allows for passage of additional catheters through the port body.

The septum 18 is shaped so that flow between the needle 20 and the reservoir 16 is increased over that of ports of the prior art. Additionally the septum 18 may be shaped so that regions of low flow within the port 10 where coagulation may occur is reduced relative to ports of the prior art. FIGS. 10 and 11 show two embodiments of the septum 18 of the present invention.

One method by which increased flow is accomplished is shown in FIG. 10. The reservoir side 40 of the septum 18 is concave so that it smoothly completes the upper surface of the reservoir 16 and generally mirrors the bottom 42 of the reservoir 16, resulting in an oval cross-sectional shape.

In the septum 18 of FIG. 11, the reservoir side 44 is also concave to complete the upper surface of the reservoir 16. It also has a dimple 52 that generally mirrors the bottom 46 of the reservoir 16, resulting in a cross-sectional shape that will minimize the volume in the central region of the reservoir 16 where blood flow is reduced and coagulation may occur. Additionally, the septum facilitates sealing.

The area of the port body 14 surrounding the septum 18 is designed so that the location of the septum 18 is tactilely identifiable through the skin. This is achieved in one embodiment by raising the edge 50 of the port body 14 surrounding the septum 18 above the level of the septum 18, as can be seen in FIGS. 4 and 10. The edge 50 may be rounded with a radius that is small enough so it can be easily sensed through the skin. However, the radius needs to be large enough so that it fits comfortably and will not work its way through the skin over time.

Figure 7:
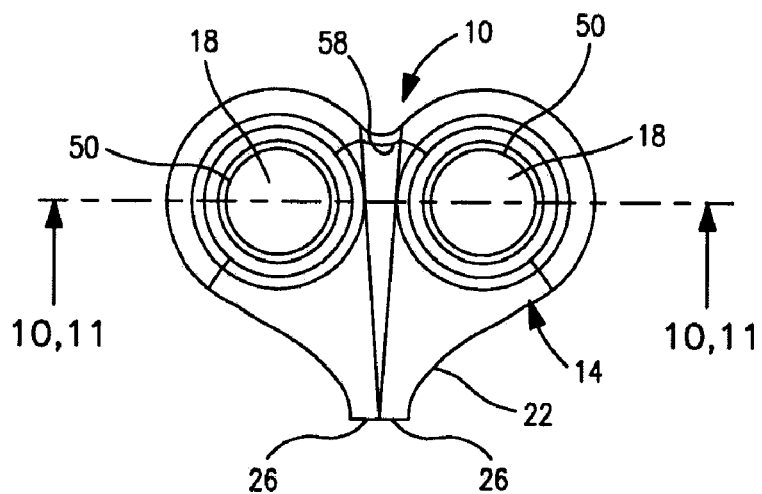
FIG. 7 is a top plane view of the port of FIG. 4.
Figure 8:
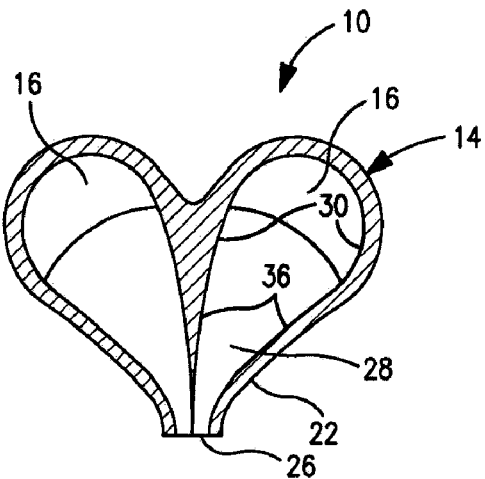
FIG. 8 is a cross-sectional view of one embodiment of the dual port device taken along the line 8-8 of FIG. 6.

Optionally, as shown in FIG. 7, the port 10 has one or more suture holes 58. The suture holes 58 are optionally filed with silicone so that if a hole 58 is not pierced by a suture needle, it remains filled. In other aspects, a suture flange may be affixed or constructed into the port device. For example, the flange may be arranged circumferentially arranged such that, in a single port design, the flange may be arranged from one side of the distal tip of the outlet longitudinally around the port to the other side of the distal tip of the outlet. Alternatively, in a dual port device, the flange may be arranged from one side of the distal tip of the outlet longitudinally around the port to the other side of the mirrored distal tip of the outlet. In yet another embodiment, multiple shorter flanges may be arranged on the port body at specific points. The suture flange may be constructed of any suitable material, such as a biocompatible polyurethane or silicone.

The port 10 of the present invention is intended to be used with either a fixed catheter, that is a catheter that cannot be detached from the stem 22, or a detachable catheter. The stem 22 is designed to accommodate the appropriate catheter using attachments known in the art. The length of a detachable catheter can be adjusted by removing it from the port, trimming the proximal end, and reattaching it to the port. In this way, catheters with exotic tip configurations can be used. In instances where a blunt tip is sufficient, the catheter can be fixed and the length can be adjusted by cutting the distal end of catheter.

Figure 12:
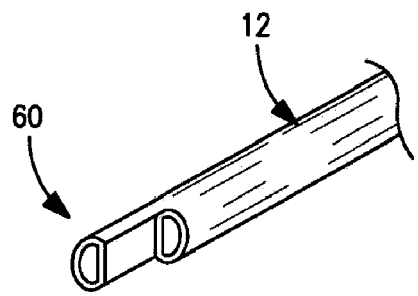
FIG. 12 is an example of the distal end of a step tip catheter.
Figure 13:
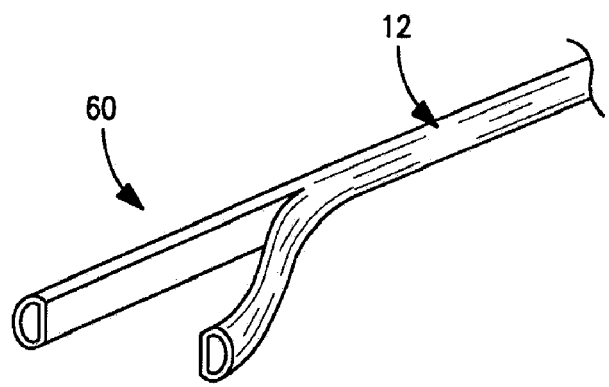
FIG. 13 is an example of the distal end of a split tip catheter.

The distal end 60 of the catheter 12 is terminated by any type of tip configuration that is desired. There are a number of tip configurations that currently exist in the hemodialysis industry including, but not limited, to the blunt tip, shown in FIG. 1, the step tip, shown in FIG. 12, and the split tip, shown in FIG. 13.

Figure 14:
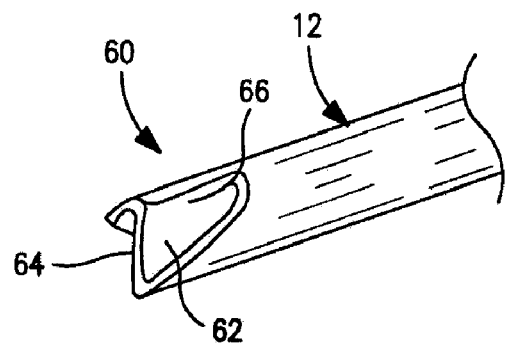
FIG. 14 is an example of the distal end of a catheter with comparable forward and reverse flow.
Figure 15:
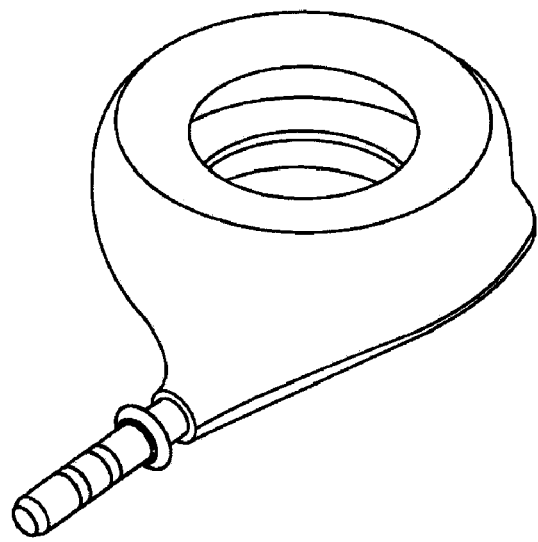
FIG. 15 is a perspective view of one embodiment of a single port device of the present invention.
Figure 16:
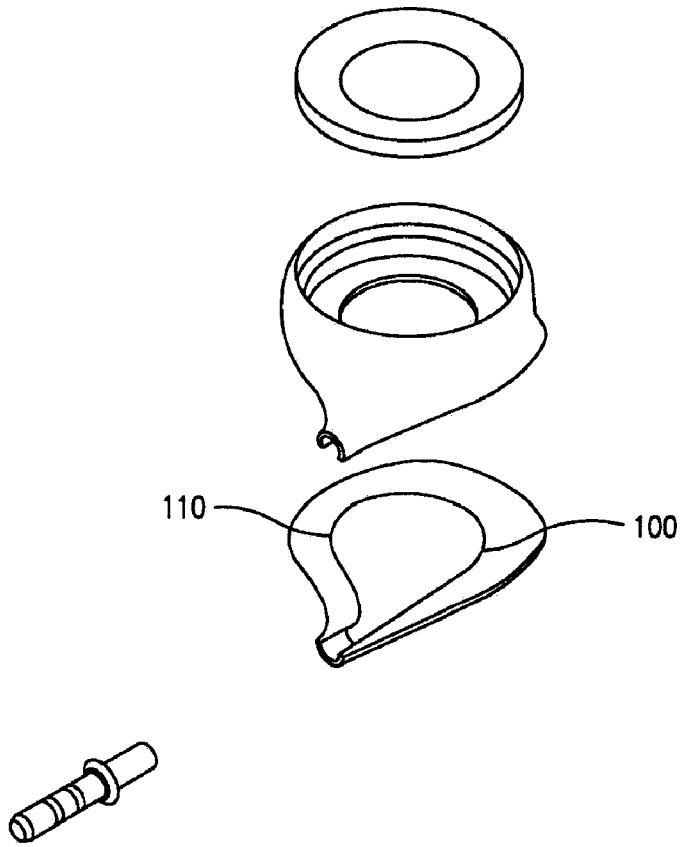
FIG. 16 is an expanded perspective view of one embodiment of a single port device of the present invention.
Figure 17:
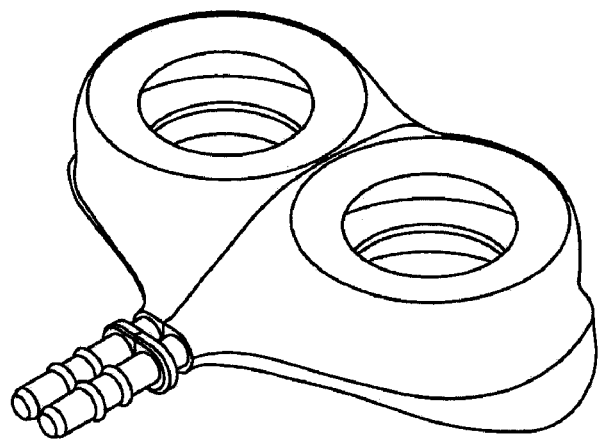
FIG. 17 is a perspective view of one embodiment of a dual port device of the present invention.
Figure 18:
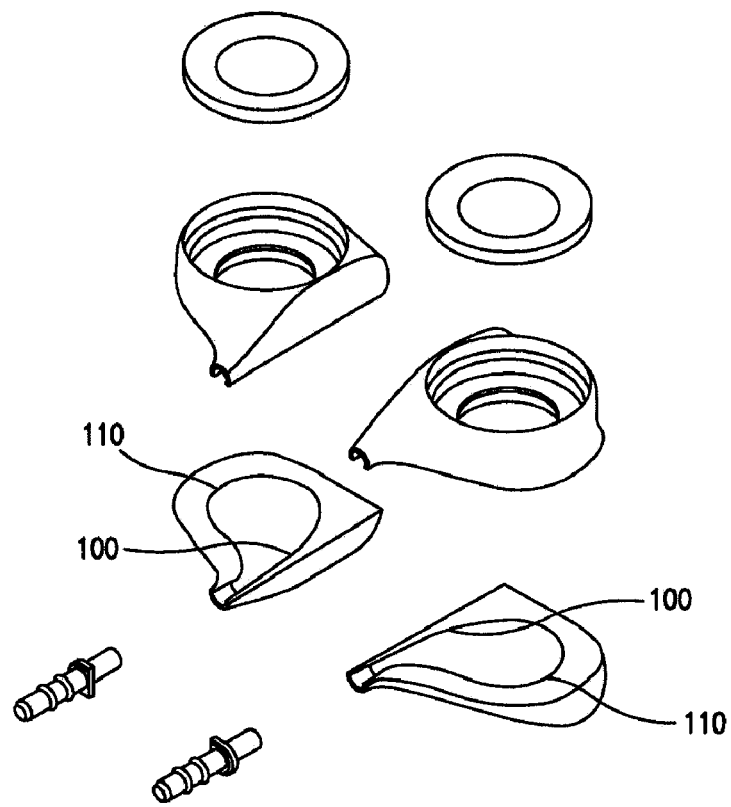
FIG. 18 is an expanded perspective view of one embodiment of a dual port device of the present invention.

Tip configurations contemplated for use by the present invention include those that have comparable forward and reverse flow. One prior art tip configuration, shown in FIG. 14, provides comparable forward and reverse flow by having symmetrical cutouts 62, 64 on opposite sides of the catheter 12. Fluid leaving cutout 64 exits in a jet carrying it far from the catheter 12 before it is available for recirculation into cutout 62. In the same instance blood entering cutout 62 enters at the most proximal point 66 of cutout 62 enabling the maximum separation of the inlet and outlet streams of fluid.

Optionally, the diameter of the catheter 12 decreases along its length from the proximal end in order to improve flow, to improve the seal of the vascular puncture 11 around the catheter 12, or to reduce the propensity for kinking of the catheter 12.

Figure 22:
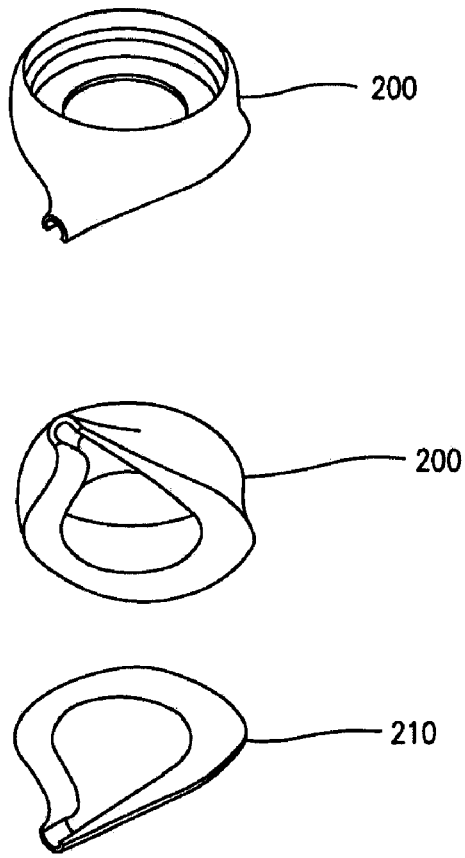
FIG. 22 is an expanded perspective view of one embodiment of a single port device including both top (a) and bottom (b) perspective views of the upper piece.

Conventional methods for fabricating vascular access devices employ a method in which the entire reservoir of the port is hollowed out from a single piece of stock. For example, the port body is not fabricated from at least two pieces and joined together to define the reservoir and outlet, wherein one of the pieces is not the septum. For example, an upper 200 and lower piece 210 of the port body is fabricated separately as shown in FIG. 22. FIG. 22 shows an upper and lower piece each fabricated separately and then joined together to define the shape of the reservoir and outlet. A septum may also be used to extend the defined shape of the reservoir and outlet and also include additional shape features such as dimples or other corrugated patterns. However, in a preferred aspect, the septum is shaped so that the entire upper surface of the chamber defined by the reservoir/outlet is identical and mirrors the lower surface.

Accordingly, in one aspect the vascular access device of the present invention is made by a process including separately forming at least two separate pieces; and joining the pieces together thereby defining the surface of the reservoir and outlet. The pieces that are separately fabricated and joined may be derived by slicing the port design along any axis to produce, for example, two pieces. Likewise, additional slices of the port design may produce more than two pieces (for example, quarters or eighths or the like). In a preferred aspect, the port design is sliced once latitudinally producing an upper piece 200 and a bottom piece 210 that are to be fabricated separately as shown in FIG. 22.

The pieces may be formed from a variety of materials suitable for implantation and formed by methods appropriate to the material used.

Thus it has been shown and described an implantable catheter port which satisfies the objects set forth above.

The following examples are intended to illustrate but not limit the invention.

Example 1

Flow Visualization of Port Designs

This example illustrates the superior flow rate characteristics of the tapered and tangential port design of the present invention. A Flow Visualization Experiment (FVE) was conducted showing the benefits of a tangent and tapered outlet port design versus both a tangent but not tapered outlet port design and a centered outlet port design typically used in the art.

The following port configurations were utilized to conduct the FVE. A tangent and tapered (TT) port design was constructed having a chamber volume of 0.742 ml and having a hydraulic diameter of the outlet (4 times the area of the outlet divided by the perimeter of the outlet) of 2.073 mm. The tangent and tapered design is shown in FIG. 19 wherein R1 is approximately 0.85 inches and R2 is approximately 0.4 inches.

Figure 23:
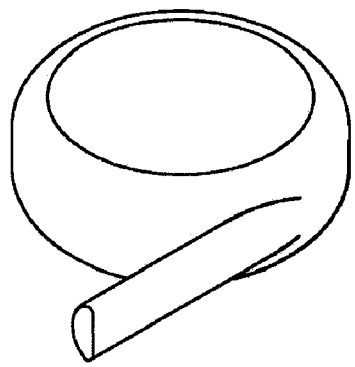
FIG. 23 shows a single port device in a tangential not tapered configuration.
Figure 24:
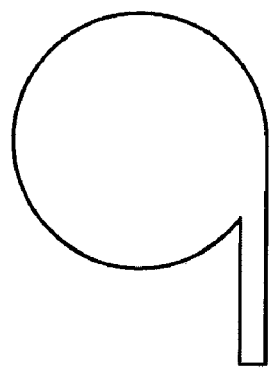
FIG. 24 shows the reservoir and outlet design of a single port device in a tangential not tapered configuration.

A tapered not tangent (TNT) port design was constructed having a chamber volume of 0.847 ml and having a hydraulic diameter of the outlet (4 times the area of the outlet divided by the perimeter of the outlet) of 1.729 mm. The tangent not tapered design is shown in FIGS. 23 and 24.

Figure 25:
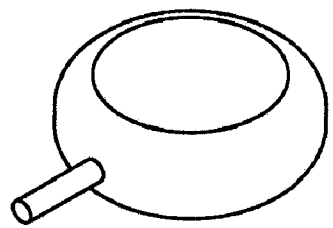
FIG. 25 shows a single port device in a centered not tapered not tangential configuration.
Figure 26:
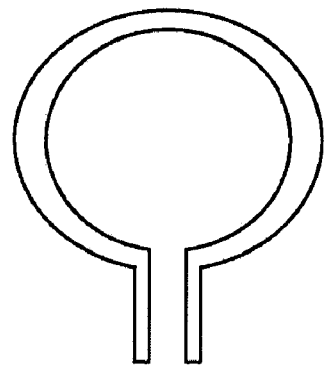
FIG. 26 shows the reservoir and outlet design of a single port device in a not tapered and not tangential configuration.

A centered tapered (C) port design was constructed having a chamber volume of 0.766 ml and having a hydraulic diameter of the outlet (4 times the area of the outlet divided by the perimeter of the outlet) of 1.168 mm. The center tapered design is shown in FIGS. 25 and 26.

The FVE was conducted using the above described port designs in the following stepwise fashion.

Step 1: A hollow, cylindrical, and blunt tipped needle was inserted into a transparent tangent and tapered port reservoir filled with blue water based ink via an affixed septum of a design that minimizes the amount of intrusion of the septum into the reservoir.

Step 2: Water was then pumped through the needle into the reservoir at a prescribed flow rate of 10, 40, 150, or 300 ml/min while a 30 frame-per-second video camera monitored and recorded the visualization of the flow.

Step 3: The recorded video was then loaded into a numerical analysis software, where the intensity of the pixels of each frame of the video was stored in a matrix.

Step 4. For each frame in the video, the intensity of each pixel in a single frame was summed.

Step 5. The sums of the intensities of all frames for a given flow rate were then plotted as a function of time along with expected values for the predicted intensities for that same given flow rate as predicted by, $$X = Ce^{(-\frac{F}{V} \cdot t)}, \quad (1)$$

where X is the sum of the intensities, C is the starting intensity, F is the flow-rate of water into the reservoir, V is the volume of the reservoir, and t is the elapsed time and Equation (1) is the solution to the differential equation which represents perfect mixing within the reservoir, $$\frac{dX}{dt} + \frac{F}{V} \cdot X = 0. \quad (2)$$

Step 6. The times at which the sum of the measured pixel intensities has $e^{-1}$, $e^{-2}$, and $e^{-3}$ percent of the initial amount of pixel intensity remaining was then taken from the plot and compared to the pixel intensities of each respective decrement as predicted by equation (1).

Step 7. The difference between the expected time of each decrement and the actual time of each decrement was then compared.

Step 8. This procedure was repeated for each port design.

Figure 27:
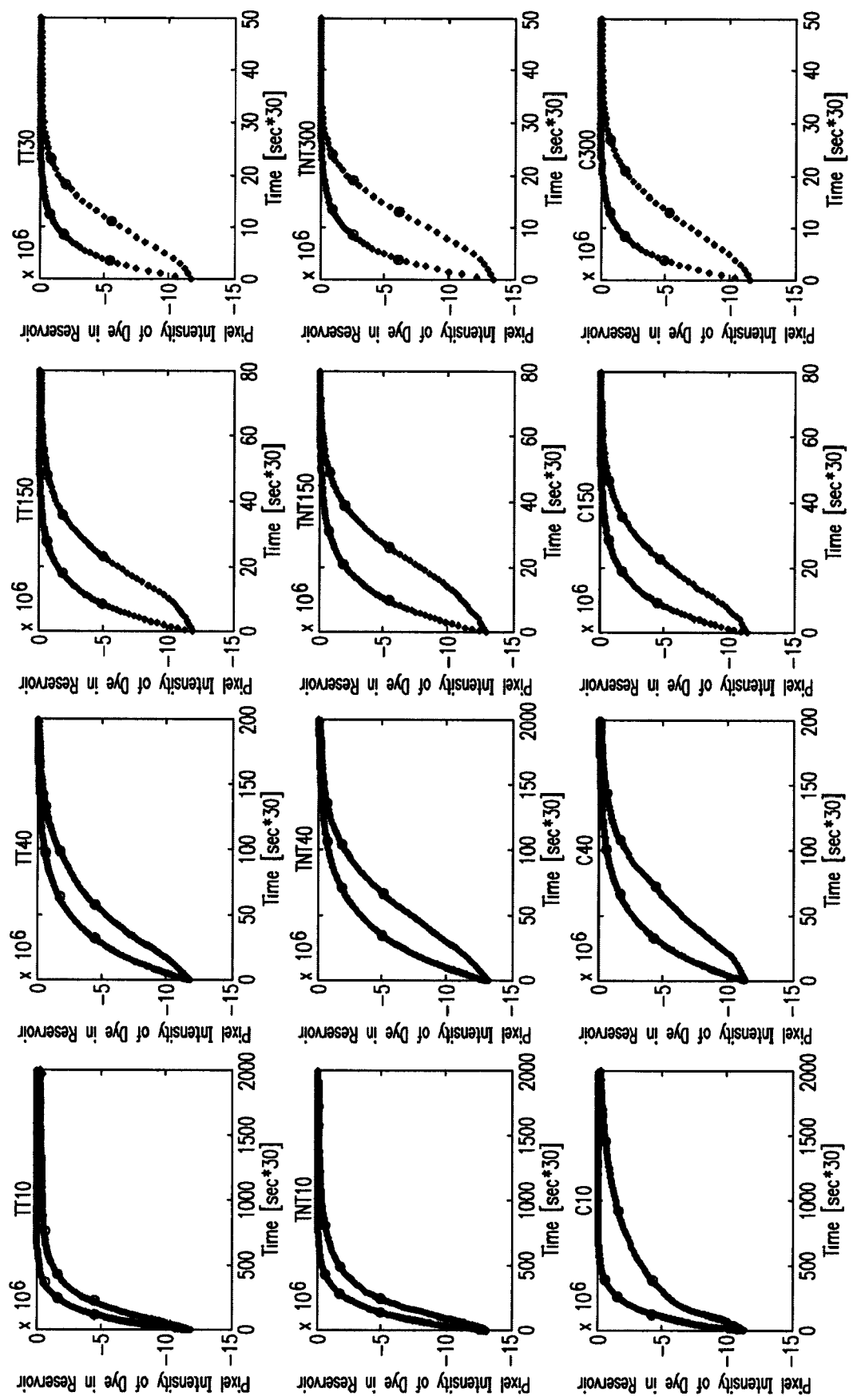
FIG. 27, shows a series of graphs for each of three different port designs of the results of a Flow Visualization Experiment (FVE). The graphs plot pixel intensity of dye in the reservoir versus a given time frame.
Figure 28:
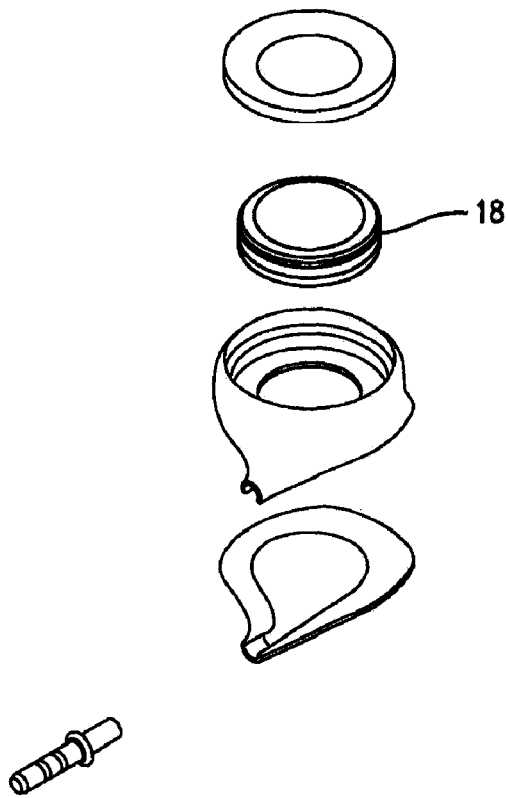
FIG. 28 is an expanded perspective view of one embodiment of a single port device of the present invention including a septum 18.
Figure 29:
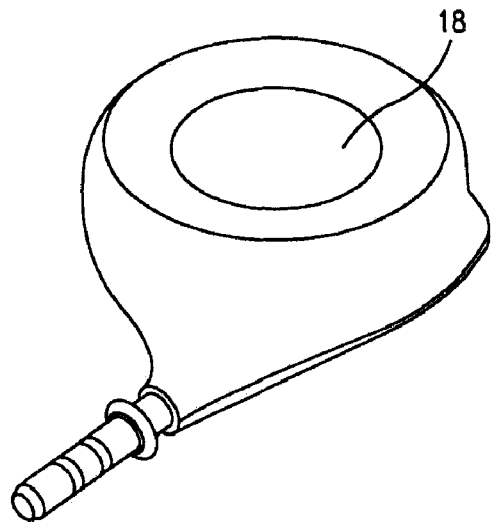
FIG. 29 is a perspective view of one embodiment of a single port device of the present invention including a septum 18.
Figure 30:
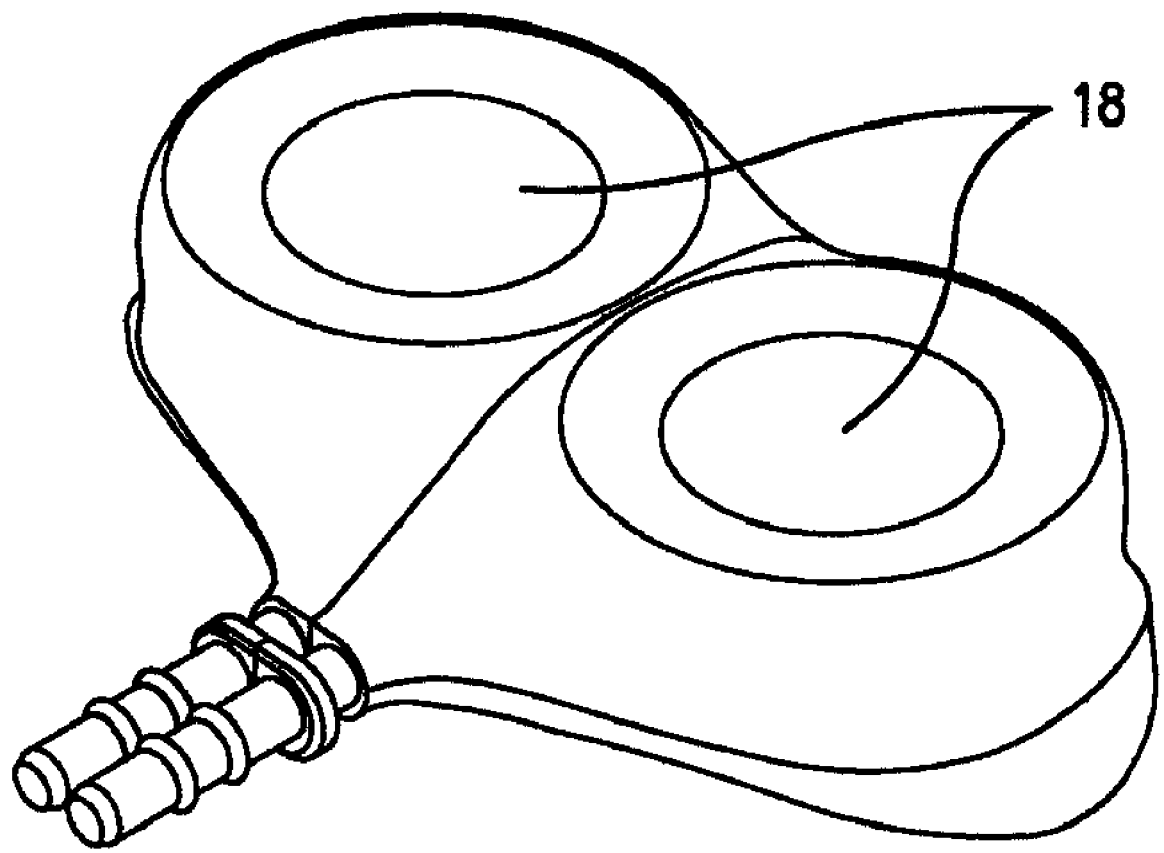
FIG. 30 is a perspective view of one embodiment of a dual port device of the present invention including septums 18.

FIG. 27, shows a series of four graphs for each port design (TT, TNT and C) plotting pixel intensity of dye in the reservoir versus a given time frame. The two lines of each graph show the difference between the expected time of each decrement and the actual time of each decrement as determined by the above described method. Data points plotted on the individual graphs were generated consistently for each graph.

The FVE demonstrates that the tangent and tapered outlet port design minimizes the difference between the measured and the expected decrement times for the flow rates, particularly flows of 10 and 40 ml/min.

This measure of improvement in flow is of particular value because low flow-rates, such as 10 and 40 ml/min, are representative of three important vascular access therapies or procedures: 1) fluid removal from fluid overloaded patients having Congestive Heart Failure (CHF); 2) the flushing of a subcutaneous port by hand and 3) the injection of chemotherapeutic agent by hand or by gravity.

Fluid may be extracted from fluid overloaded congestive heart failure patients by implanting a port of tangent and tapered outlet design and removing blood from one reservoir and replacing it through the other reservoir at a flow rate of between 10 and 40 ml/min.

As demonstrated by the minimal difference of the decrements (theoretical versus actual) the tangent and tapered outlet port observes closer to perfect mixing within the reservoir, which corroborates the appearance of fewer dead-flow zones in the original videos of the experiment.

With the presence of fewer dead zones it is expected that in a blood transfer application, such as that of fluid removal from CHF patients, a port having a tangent and tapered outlet is expected to have a longer patency, as the propensity for thrombosis is expected to be proportional to the presence of dead zones.

Better mixing within the reservoir, as indicated by lower decrement times, is also very important for achieving a good flush for clearance of the port, which is important for increasing the patency of ports. Typically, a nurse can inject fluid at a flow rate of up to approximately 10 ml at 40 ml/min by hand. Thus having better port clearance at low flow rates is critically important.

Although the invention has been described with reference to the above example, it will be understood that modifications and variations are encompassed within the spirit and scope of the invention. Accordingly, the invention is limited only by the following claims.

What is claimed is:

1. A subcutaneous access device including a port body comprising:
    (a) a reservoir; and
    (b) an outlet having a proximal tip joined to the reservoir and a distal tip, wherein the shape of the reservoir and the outlet are defined by the inner surface of the port body;
    wherein the reservoir and the outlet are in fluid communication and defined by an inner sidewall and an outer sidewall forming lateral boundaries in opposition defining a flow passage along the reservoir to the distal tip of the outlet;
    wherein the lateral boundaries transition into an upper surface of the reservoir and a bottom surface of the reservoir via a smooth curve; and
    wherein further the inner sidewall is globally tangent along the reservoir surface and the outer sidewall is tapered and transitions from the reservoir to the outlet defined by a radius of curvature R1 having an angle θ that is greater than 90° and up to 225°, which curvature R1 transitions at the proximal tip of the outlet into a curvature R2 extending to the distal tip of the outlet.

2. The device of claim 1, wherein the device comprises at least two port bodies.

3. The device of claim 2, wherein the device consists of two port bodies.

4. The device of claim 2, wherein the flow passage of each port body is identical and the port bodies are configured as mirror images.

5. The device of claim 1, further comprising a catheter.

6. The device of claim 5, wherein the catheter is tapered along the length of the catheter.

7. The device of 5, wherein the catheter is tapered from the port body outlet to the tip of the catheter.

8. The device of claim 1, wherein the device further comprises a self-sealing septum.

9. The device of claim 1, wherein the reservoir is circular or elliptical.

10. The device of claim 1, wherein the port body comprises a bottom piece and a top piece.

11. The device of claim 10, wherein the bottom piece consists of a single material.

12. The device of claim 10, wherein the top piece consists of a single material.

13. The device of claim 1, wherein the device further comprises a suture flange.

14. The device of claim 1, further comprising an internal coating.

15. The device of claim 1, wherein R1 is about 0.85 inches and R2 is about 0.4 inches.

16. The subcutaneous access device of claim 1, wherein each port body is made by a process comprising:
    (a) separately forming at least two pieces; and
    (b) joining the at least two pieces together thereby defining the surface of the reservoir and outlet.

17. The device of claim 16, wherein the top and bottom pieces are of unitary construction.

18. The device of claim 17, wherein the top and bottom pieces are formed from the same material.

19. The device of claim 16, wherein the port consists of two pieces.

20. The device of claim 19, wherein the two pieces are an upper piece and a bottom piece.

21. A subcutaneous access device comprising two port bodies, each port body comprising:
    (a) a reservoir; and
    (b) an outlet having a proximal tip joined to the reservoir and a distal tip, wherein the shape of the reservoir and the outlet are defined by the inner surface of the port body;
    wherein the reservoir and the outlet are in fluid communication and defined by an inner sidewall and an outer sidewall forming lateral boundaries in opposition defining a flow passage along the reservoir to the distal tip of the outlet;
wherein the lateral boundaries transition into an upper surface of the reservoir and a bottom surface of the reservoir via a smooth curve; and
wherein further the inner sidewall is globally tangent along the reservoir surface and the outer sidewall is tapered and transitions from the reservoir to the outlet defined by a radius of curvature R1 having an angle θ that is greater than 90° and up to 225°, which curvature R1 transitions at the proximal tip of the outlet into a curvature R2 extending to the distal tip of the outlet.

22. The device of claim 21, wherein R1 is about 0.85 inches and R2 is about 0.4 inches.

23. The device of claim 21, wherein the port bodies are configured as mirror images.

\* \* \* \* \*